US006267720B1

(12) United States Patent
Knox et al.

(10) Patent No.: US 6,267,720 B1
(45) Date of Patent: Jul. 31, 2001

(54) SYSTEM AND METHOD FOR HAIR LOSS REDUCTION AND RE-GROWTH

(76) Inventors: Jo Rodney Knox, 1543 Wildrose Dr., Minden, NV (US) 89423-3902; Edward W. Smith, 464 Eagle Dr., Incline Village, NV (US) 89451-8941

( * ) Notice: Subject to any disclaimer, the term of this patent is extended or adjusted under 35 U.S.C. 154(b) by 0 days.

(21) Appl. No.: 09/553,131

(22) Filed: Apr. 19, 2000

Related U.S. Application Data
(60) Provisional application No. 60/142,520, filed on Jul. 7, 1999.

(51) Int. Cl.[7] .................................................... A61N 1/00
(52) U.S. Cl. ................................................................ 600/15
(58) Field of Search ............................................ 600/9–15

(56) References Cited

U.S. PATENT DOCUMENTS

| | | |
|---|---|---|
| 4,549,532 | 10/1985 | Baermann . |
| 5,092,835 | 3/1992 | Schurig et al. . |
| 5,116,304 | 5/1992 | Cadwell . |
| 5,251,623 | 10/1993 | Groux et al. . |
| 5,304,111 * | 4/1994 | Mitsuno et al. .......................... 600/9 |
| 5,415,617 | 5/1995 | Kraus . |
| 5,595,564 | 1/1997 | Pinna . |
| 5,720,046 * | 2/1998 | Lopez et al. ............................ 600/15 |
| 5,871,438 * | 2/1999 | Ardizzone .............................. 600/15 |

FOREIGN PATENT DOCUMENTS 05258817  10/1995  (JP) .

OTHER PUBLICATIONS

W. Stuart Maddin, M.D., et al., "The Biological Effects of a Pulsed Electrostatic Field with Specific Reference to Hair," Pharmacology and Therapeutics, Division of Dermatology, Univ of British Columbia School of Medicine, Jul.–Aug., 1990, vol. 29, No. 6.*

Stanley H. Kornhauser, Ph.D., et al., "ETG–Electrotrichogenesis," American Journal of Electromedicine, Dec. 1992.*

W. Stuart Maddin, M.D., et al., "Electrotrichogenesis: Further Evidence of Efficacy and Safety on Extended Use," Pharmacology and Therapeutics, Div. Of Dermatology, Univ. of British Columbia School of Medicine, Dec. 1992, vol. 31, No. 12.*

Pamela Fayerman, "A Hair–raising Story", The Vancouver Sun, Monday, Jul. 21, 1997.*

* cited by examiner

Primary Examiner—John P. Lacyk
(74) Attorney, Agent, or Firm—Kenehan & Lambertsen; John C. Lambertsen

(57) ABSTRACT

Removable headwear is provided for therapeutically applying a permanent magnetic field to hair follicles located in the scalp to retard hair loss and promote hair re-growth. A flexible sheet of magnetic material having a plurality of alternating north-south poles is placed with a head covering that is in turn placed upon the head of a subject. Such head covering, while suitable for nighttime wear, may not be deemed socially acceptable for wear during the day. To enable the subject to maximize the exposure of the scalp to the magnetic fields, the head covering is configured to permit an item of conventional headwear to be placed over and cover the inner head covering.

24 Claims, 1 Drawing Sheet

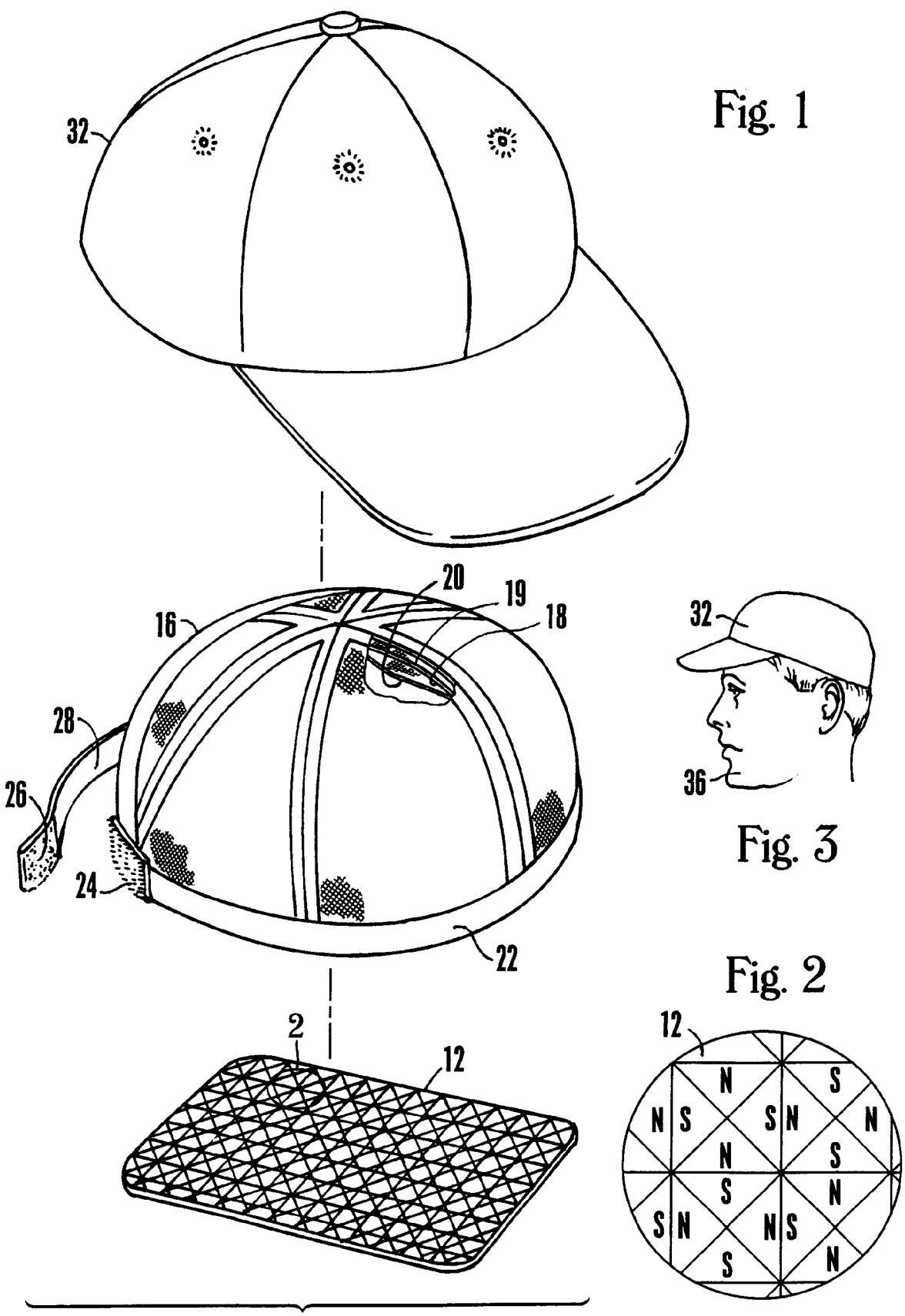

SYSTEM AND METHOD FOR HAIR LOSS REDUCTION AND RE-GROWTH

CROSS-REFERENCE TO RELATED APPLICATION

This application claims the benefit of U.S. Provisional Application, Ser. No. 60/142,520, filed Jul. 7, 1999.

BACKGROUND OF THE INVENTION

1. Field of the Invention

The present invention relates to therapeutic devices and, more particularly, to such devices as utilize the application of a static magnetic field to stimulate the operation and repair of damaged human tissue. More specifically, the present invention relates to a head covering that includes a bipolar magnetic sheet that when worn by a user stimulates hair follicles to retard further hair loss and/or stimulate additional hair growth.

2. Description of the Prior Art

Electromedicine is a type of "energy medicine" (also known as "vibrational medicine") employing electromagnetic fields that is based upon the belief that such fields control or influence all living organisms. The health benefits of electromedicine, including the use of magnets, have been touted for centuries. As early as 200 B.C. the Greek physician Galen described medical applications using "static" or "permanent" (non-time varying) magnets. Around 1000 A.D. Ali Abbas, a Persian physician, used magnetism to relieve "spasms" and "gout." (See, Buryl Payne, *The Body Magnetic*, 5th Edition, 1991). In 1766 Anton Mesmer wrote of the benefits and anecdotal experiences of using magnets for a wide variety of ailments.

Magnetic fields are related to electric fields, as was first shown by Hans Oersted in 1819. James Clerk Maxwell later formalized this relationship between magnetic and electric forces in four elegant equations. For purposes of the present application, the most important of these relationships of Maxwell speaks to the generation of an electric current within a conductor where the conductor is moved through a static magnetic field created by a permanent magnet.

This relationship is crucial to the present invention, because most historical applications of electromedicine have been directed towards or make use of time-varying electric fields. Health applications of magnetic fields, particularly permanent magnetic fields, have been essentially ignored, remaining as "folk remedies" or anecdotal healing aids.

This backwater status is difficult to understand, since a time-varying electric field engenders a time-varying magnetic field. While science has yet to determine if there is a separate beneficent effect owing to either the electric or magnetic fields, the use of these pulsed electromagnetic fields (PEMFs) is the primary focus of electromedicine today.

This work has progressed to the utilization of PEMFs for the prevention of hair loss and stimulation of hair re-growth using a process called Electrotrichogenesis (ETG) For a further discussion, see Maddin, et al., "The Biological Effects of a Pulsed Electrostatic Field with Specific Reference to Hair: Electrotrichogeneisis", University of British Columbia, Division of Dermatology, July-August, 1990, Vol 29, No. 6. ETG clinical trials at the University of British Columbia in 1989, and repeated again in 1992, were successful: Of the 30 men enrolled in the trial with the ETG machine, 29 either experienced no further hair loss or some re-growth after 36 weeks of trials. (See Maddin, et al, "Electrotrichogenesis: Further Evidence of Efficacy and Safety on Extended Use", International Journal of Dermatology, Vol, 31, No. 12, December 1992.)

The principal researcher, however, acknowledges that the exact beneficial mechanism is unclear. The researcher proposes an extension of the work in non-united fractures of Becker and Selden (Becker, R.O Selden, G., The Body Electric: Electromagnetism and the Foundation of Life, New York, Quill 1985, 163–180), wherein certain cell groups were sensitive to certain frequencies and strengths of PEMFs and exhibited re-growth of bone and tissue. The extension suggested by the researcher was that the dormant follicle cells groups are similar to the fibroblast cell groups identified by Becker and Selden, and are thus capable of regeneration.

The present invention proposes a similar extension of the work of Becker and Selden. A static magnetic field from a permanent magnet, and specifically a "bi-polar" permanent magnet, meaning spatially alternating north and south magnets or magnetized areas, creates an electrophysiologic process in which the stimulation of follicle cell groups may retard loss and promote re-growth.

Prior art in the arena of reduction of hair loss and hair re-growth is for the most part directed to chemical solutions, such as minoxidil, a topical ointment applied to the affected areas of hair loss. The alternating electromagnetic field (ETG) solution is proposed by Groux, et al., in U.S. Pat. No. 5,251,623 and in Pinna, U.S. Pat. No. 5,595,564.

In '623 Groux and '564 Pinna claim a system which is based on an electrical pulse generator, and not a permanent magnet. Other prior art devices similar to Penna '564 are Kraus (U.S. Pat. No. 5,415,617), wherein an applicator coil is proposed for alternating field electromagnetic therapy of a shoulder or an arm; Cadwell (U.S. Pat. No. 5,116,304) proposing a skullcap-shaped coil that is energized to produce an alternating electromagnetic field for stimulating deeply located neurons of a human cranium. There is no suggestion or disclosure in any of this prior art towards using a permanent magnetic field as the primary efficacious element.

The inventors are aware of at least one other patent relating to a permanent magnet application to the human head. In U.S. Pat. No. 5,092,835 to Shurig, et al., an integrated auditory/visual/electrode system is described having a cap that is provided with a number of permanent magnets. These magnets generate a magnetic energy strength that is designed to apply a " . . . magnetic field of constant intensity to the brain of said subject . . . ". This differs from the present invention in a number of respects.

The present invention has no requirement or need to have any magnetic field penetrate the skull, or to provide stimuli to the brain. The structure of Shurig, et al., (the '835 patent) is intended to stimulate the brain with magnetic energy, which may or may not provide stimulation of the hair follicles as is taught by the present invention. A magnetic field proposed by the '835 patent may not be of sufficient gauss strength, north/south pole alignment or of physical orientation to provide the magnetic energy required to regenerate the cell groups in the hair follicles in those common areas of human hair loss.

Another permanent magnet-related patent, U.S. Pat. No. 4,549,532, suggests a flexible magnetic sheet having magnetic poles of alternating polarities for therapeutic use. This is taught as an improvement over earlier magnetic sheets, the alternating polarities making placement and orientation on the body less important. Such alternating polarities of the magnetic fields are said to be particularly beneficial in peripheral skin regions. There is no suggestion to placement on or about the scalp, or suggestion for the therapeutic application of magnetic energy towards the retardation of hair loss or promotion of hair re-growth. Such "therapeutic use" as is defined in the '532 patent is " . . . characterized by alleviation and removal of pain . . . ".

Discounting the "snake oil" remedies, there are multiple problems posed by the presently used techniques for addressing the problem of hair loss. The demand for a solution is so great, that any technique showing a documentable sign of promise seems to bear a high price tag. Whether through drug therapy or surgical technique(s), such treatments are expensive, and, in the case of surgery, involve great inconveniences for the patient. Drug therapy is less site specific, and presents the hazards of documented side effects. It would be desirable to provide an inexpensive treatment regime to retard or reverse hair loss that is non-invasive, and that does not require reliance on the taking or topical application of pharmaceutical preparations having possible systemic affects.

SUMMARY OF THE INVENTION

It is an object of the present invention to provide a non-consumable, non-invasive product that is adaptable to be worn by any user during the day or at night—or both. In this regard, a bi-polar magnetic insert is sewed into the crown of a soft mesh cap. When worn in public, the insert and cap are dimensioned to allow an outer cap, such as a baseball cap, to be placed over and conceal the inner mesh cap.

Use of the cap/magnetic insert combination enables the user to maintain the magnetic field in close proximity over extended periods of time to those areas of the body that are at risk of hair loss, with a minimal disruption to the user's lifestyle.

In use, the soft mesh cap is placed over the head of a user, and is worn in much the same manner as were night caps in earlier times. While being worn, the magnetic sheet lies in close proximity to the wearer's scalp, maintaining in place the magnetic fields of alternating polarities with respect to those layers of the outer skin having the hair follicles and supportive circulatory system. The mesh cap is considered acceptable by most people for nighttime wear, and, as mentioned previously, a baseball-type cap can easily cover the soft mesh cap during the day. The ability to wear the magnetic sheet in close proximity to the scalp for virtually the entire day greatly increases the likelihood of obtaining a desired result over the significantly less convenient treatment regimens of the prior art.

Some further objects and advantages of the present invention shall become apparent from the ensuing description and as illustrated in the accompanying drawings.

BRIEF DESCRIPTION OF THE DRAWINGS

FIG. 1 is an exploded perspective view of a magnetic sheet of alternating polarity as received within a pair of caps suitable for being worn on an around-the-clock basis by a user in accordance with the present invention;

FIG. 2 is a partial, enlarged plan view, with schematics added, taken within circle 2 of FIG. 1 showing a magnetic sheet of alternating polarities in accordance with the present invention; and FIG. 3 is a perspective view showing a user having in place the caps and magnetic sheet in accordance with the present invention.

DETAILED DESCRIPTION OF THE PREFERRED EMBODIMENTS

Reference is now made to the drawings wherein like numerals refer to like parts throughout. In FIG. 1 a magnetic sheet 12 is received within an inner cap 16. Although not shown in the Figures, the magnetic sheet 12 can be directly attached to a lining of the inner cap 16 or, more preferably, is placed within an inner sleeve 18 formed in an inner lining of the inner cap 16. Upon such placement, that portion of the inner cap lining underlying the inner sleeve 18 forms a treatment surface 20. In any event, regardless of its manner of attachment or enclosure, for purposes of the present invention the magnetic sheet 12 is received by and held within the inner cap 16 to obtain proper positioning of the magnetic fields associated with the magnetic sheet 12.

The inner cap 16 is preferably provided with an adjustable headband 22, permitting its use over a variety of different head sizes. In the depiction of FIG. 1, a hook-and-loop fastening system can provide such adjustability, consisting of a loop section 24 formed on an outer surface of the headband 22 with a hook section 26 located on an adjustment band 28.

As is also shown in FIG. 1, an outer cap 32 may optionally be placed over the inner cap 16 on such occasions where the appearance of the inner cap 16 is not deemed to be appropriate by a user (not shown in FIG. 1). The style of the outer cap 32 can be of any conventional cap or hat design, with a baseball-type design shown in FIG. 1. Regardless of the particular design chosen, the purpose of the outer cap 32 is one of concealment—relative to the inner cap 16.

FIG. 2 illustrates an enlarged view of the magnetic sheet 12, with the polarities of the magnetic fields schematically depicted. A plurality of magnetized areas are formed over the magnetic sheet 12 in a manner whereby adjacent areas are of opposite magnetic polarity. As is illustrated in FIG. 2, areas showing "North" polarity lay adjacent areas of "South" polarity.

In FIG. 3 a user 36 is shown wearing the outer cap 32. As previously noted, the purpose of the outer cap 32 is to conceal use of the inner cap 16 holding the magnetic sheet 12. To all outward appearances, the user 36 in FIG. 3 looks identical with any number of persons in our society that embody the "baseball cap" look. Of course, in other situations, a different outer cap might be more appropriate, such as a "cowboy" hat, a derby, or beret. It is also possible, although not shown in the Figures, to make use of a toupee as the inner (and only) "covering" or "applicator"—with the magnetic sheet 12 held within the inner lining or otherwise attached to the toupee.

The present invention preferably uses a magnetic sheet fabricated out of ELASTOMAG™ such as that manufactured by Nikken, Inc., of Irvine, Calif., under the name Elastomag™ Vest, Model 1668. For most applications, the magnetic sheet will measure 3" by 4¾" and is 1¹⁄₁₆" in thickness. The inner cap 16 is preferably a multi-layer mesh cap, such as a custom made pro-style polymesh seamed front offered by Headmaster, Inc., of Santa Ana, Calif. As mentioned previously, the preferred manner of pairing the magnetic sheet and the inner cap is by placement of the magnetic sheet into a sleeve formed in a lining of the inner cap. The outer cap is of conventional design and size(s), such as the models manufactured by Headmaster, Inc. (see above).

Our invention has been disclosed in terms of a preferred embodiment thereof, which provides an improved manner of applying magnetic fields of alternating polarities to the scalp of a user to retard or reverse hair loss that is of great novelty and utility. Various changes, modifications, and alterations in the teachings of the present invention may be contemplated by those skilled in the art without departing from the intended spirit and scope thereof. It is intended that the present invention encompass such changes and modifications.

We claim:

1. A removable headwear assembly of an inner applicator cap and an outer cosmetic cap for therapeutic use by application of static magnetic fields to a human scalp of a subject comprising:

permanent magnetic means for stimulation of the scalp;

an inner applicator receiving said magnetic means in a manner forming a treatment surface therein, said applicator having a peripheral edge that defines a headband, said headband and said applicator together forming a head-receiving cavity;

attachment means for securing the magnetic means to the applicator;

means for adjusting the fit of the applicator to the head; and means for attaching the outer cap to the applicator to form a cosmetic assembly suitable for daytime wear.

2. A removable headwear assembly according to claim 1 wherein the magnetic means is a flexible sheet of magnetic material, magnetized to create a pattern of alternating magnetic polarities that extend substantially across the surface of said flexible sheet.

3. A removable headwear assembly according to claim 2 comprising only the head-worn inner cap having permanent magnetic means for stimulation of the scalp, suitable for nighttime wear, attachment means for securing the magnetic means to the inner cap, and means for adjusting the fit of the inner cap to the head.

4. A removable headwear assembly according to claim 1 comprising only the outer cap having permanent magnetic means for stimulation of the scalp, suitable for cosmetic daytime wear, attachment means for securing the magnetic means to the outer cap, and means for adjusting the fit of the outer cap to the head.

5. A removable headwear assembly according to claim 1 wherein the magnetic means is a flexible sheet of magnetic material, magnetized to create a uniform magnetic polarity that extends substantially across the surface of said flexible sheet.

6. A removable headwear assembly according to claim 5 comprising only the head-worn inner cap having permanent magnetic means for stimulation of the scalp, suitable for nighttime wear, attachment means for securing the magnetic means to the inner cap, and means for adjusting the fit of the inner cap to the head.

7. A removable headwear assembly according to claim 5 comprising only the outer cap having permanent magnetic means for stimulation of the scalp, suitable for cosmetic daytime wear, attachment means for securing the magnetic means to the outer cap, and means for adjusting the fit of the outer cap to the head.

8. A removable headwear assembly according to claim 1 wherein the magnetic means is a flexible sheet of substantially non-magnetic material which secure a pattern of individual magnets, with each magnet adjacent to a magnet of opposite polarity, with said pattern extending substantially across the surface of said flexible sheet.

9. A removable headwear assembly according to claim 8 comprising only the head-worn inner cap having permanent magnetic means for stimulation of the scalp, suitable for nighttime wear, attachment means for securing the magnetic means to inner cap, and means for adjusting the fit of the inner cap to the head.

10. A removable headwear assembly according to claim 8 comprising only the outer cap having permanent magnetic means for stimulation of the scalp, suitable for cosmetic daytime wear, attachment means for securing the magnetic means to the outer cap, and means for adjusting the fit of the outer cap to the head.

11. A removable headwear assembly according to claim 1 wherein the magnetic means is a flexible sheet of substantially non-magnetic material which secure a pattern of individual magnets, with each magnet adjacent to a magnet of like polarity, with said pattern extending substantially across the surface of said flexible sheet.

12. A removable headwear assembly according to claim 11 comprising only the head-worn inner cap having permanent magnetic means for stimulation of the scalp, suitable for nighttime wear, attachment means for securing the magnetic means to the inner cap, and means for adjusting the fit of the inner cap to the head.

13. A removable headwear assembly according to claim 11 comprising only the outer cap having permanent magnetic means for stimulation of the scalp, suitable for cosmetic daytime wear, attachment means for securing the magnetic means to the outer cap, and means for adjusting the fit of the outer cap to the head.

14. A removable headwear for therapeutic use by application of a magnetic field to a human scalp of a subject comprising:

a flexible sheet of a permanent magnetic material having a plurality of north and south poles formed thereon; and an applicator receiving said flexible magnetic sheet in a manner forming a treatment surface therein.

15. A removable headwear according to claim 14, wherein said plurality of north and south poles on said flexible sheet comprise an array of alternating magnetic polarities.

16. A removable headwear according to claim 15, wherein said array of alternating magnetic polarities extends substantially across an entire surface of said flexible sheet.

17. A removable headwear according to claim 15, wherein an inner surface of said applicator forms a receiving pocket with an outer surface of said receiving pocket defining said treatment surface.

18. A removable headwear according to claim 17, wherein a peripheral edge of said applicator defines a headband, said headband and said applicator together defining a head-receiving cavity.

19. A removable headwear according to claim 18, and further comprising an in-line fastener attached to said headband enabling a selective linear adjustment therein.

20. A removable headwear according to claim 19, wherein said in-line fastener is a hook and loop fastener.

21. A removable headwear according to claim 18, and further comprising an outer cap of suitable dimension to be received by and overlie said applicator.

22. A removable headwear according to claim 21, wherein said outer cap is a baseball-type cap.

23. A method of stimulating hair follicles about the head of a subject comprising the steps of:

enwrapping a flexible sheet having permanent magnetic elements within a covering for a head;

placing said covering for a head with said enwrapped magnetic sheet upon the head of said subject;

wearing said covering for a head upon the head of said subject over an extended period of time after placement thereon; and removing said covering for a head from the head of said subject upon the elapse of said extended period of time.

24. A method of stimulating hair follicles according to claim 23, and further comprising the step of:

placing an additional cover for a head upon the head of said subject in a manner to overlie the initial covering for a head with said enwrapped flexible sheet having permanent magnetic elements, said additional cover for a head embodying design characteristics deemed of greater social acceptability by said subject.

* * * * *